United States Patent [19]

Christner et al.

[11] Patent Number: 5,102,422

[45] Date of Patent: Apr. 7, 1992

[54] METHODS FOR LEATHER PROCESSING INCLUDING LIQUID ENZYME FORMULATION

[75] Inventors: Juergen Christner, Bickenbach; Ernst Pfleiderer, Darmstadt-Arheilgen; Tilman Taeger, Seeheim-Jugenheim; Ursula Bernschein, Gross-Gerau, all of Fed. Rep. of Germany

[73] Assignee: Röhm GmbH, Darmstadt, Fed. Rep. of Germany

[21] Appl. No.: 152,020

[22] Filed: Feb. 3, 1988

[30] Foreign Application Priority Data

Feb. 13, 1987 [DE] Fed. Rep. of Germany ....... 3704465

[51] Int. Cl.$^5$ ............................................. C14C 1/00
[52] U.S. Cl. .................................. 8/94.15; 8/94.1 R; 8/94.16; 435/265
[58] Field of Search ................ 252/174.12; 435/188, 435/265, 267; 8/94.1 R, 94.15, 94.16; 424/94.3; 530/817

[56] References Cited

U.S. PATENT DOCUMENTS

| | | | |
|---|---|---|---|
| 3,549,495 | 12/1970 | Monsheimer et al. | 195/6 |
| 3,557,002 | 1/1971 | McCarty | 252/89 |
| 3,558,430 | 1/1971 | Monsheimer et al. | 195/6 |
| 3,623,950 | 11/1971 | Monsheimer et al. | 195/6 |
| 3,741,902 | 6/1973 | Barrett, Jr. | 252/174.12 |
| 3,781,212 | 12/1973 | Smillie | 252/174.12 |
| 3,939,040 | 2/1976 | Monsheimer et al. | 195/6 |
| 3,966,551 | 6/1976 | Monsheimer et al. | 195/6 |
| 3,986,926 | 10/1976 | Monsheimer et al. | 195/6 |
| 4,636,222 | 1/1987 | Pfleiderer et al. | 8/94.16 |

FOREIGN PATENT DOCUMENTS

| | | |
|---|---|---|
| 200519 | 6/1907 | Fed. Rep. of Germany . |
| 288095 | 11/1914 | Fed. Rep. of Germany . |
| 847947 | 11/1951 | Fed. Rep. of Germany . |
| 927464 | 4/1955 | Fed. Rep. of Germany . |
| 941811 | 10/1955 | Fed. Rep. of Germany . |
| 974813 | 2/1956 | Fed. Rep. of Germany . |
| 976107 | 2/1956 | Fed. Rep. of Germany . |
| 976602 | 2/1956 | Fed. Rep. of Germany . |
| 976928 | 2/1956 | Fed. Rep. of Germany . |
| 941680 | 3/1956 | Fed. Rep. of Germany . |
| 975095 | 5/1956 | Fed. Rep. of Germany . |
| 1022748 | 1/1958 | Fed. Rep. of Germany . |
| 1023183 | 1/1958 | Fed. Rep. of Germany . |
| 1026038 | 3/1958 | Fed. Rep. of Germany . |
| 1034317 | 5/1958 | Fed. Rep. of Germany . |
| 1120066 | 12/1961 | Fed. Rep. of Germany . |
| 1134474 | 8/1962 | Fed. Rep. of Germany . |
| 1155560 | 10/1963 | Fed. Rep. of Germany . |
| 1203416 | 10/1965 | Fed. Rep. of Germany . |
| 1211349 | 2/1966 | Fed. Rep. of Germany . |
| 1219620 | 6/1966 | Fed. Rep. of Germany . |
| 1230169 | 12/1966 | Fed. Rep. of Germany . |
| 1282837 | 11/1968 | Fed. Rep. of Germany . |
| 1282838 | 11/1968 | Fed. Rep. of Germany . |
| 1288728 | 2/1969 | Fed. Rep. of Germany . |
| 2059453 | 4/1972 | Fed. Rep. of Germany . |
| 3312840 | 10/1984 | Fed. Rep. of Germany . |
| 631486 | 8/1982 | Switzerland . |

OTHER PUBLICATIONS

Kazandjian et al., "Enzymatic Analysis in Organic Solvents" Biotechnology and Bioengineering vol. XXVIII pp. 417–21 (1986).

Zaks, et al., "Enzyme-catalyzed process in organic solvents" Proc. Natl. Acad. Science USA vol. 82, pp. 3192–96. May (1985).

*Primary Examiner*—A. Lionel Clingman
*Assistant Examiner*—John F. McNally
*Attorney, Agent, or Firm*—Curtis, Morris & Safford

[57] ABSTRACT

Liquid enzyme preparations comprising at least one anhydrous organic liquid as a vehicle for one or more enzymes and methods for using such preparations e.g. in beamhouse operations in the commercial production of leather.

6 Claims, No Drawings

METHODS FOR LEATHER PROCESSING INCLUDING LIQUID ENZYME FORMULATION

The present invention relates to liquid enzyme preparations comprising an anhydrous organic liquid as a vehicle for an enzyme, suitably together with an additive modifying the rheology of the composition, and to methods for making leather employing such preparation.

THE PRIOR ART

The industrial use of enzymes is currently generating much interest since it is regarded as the prototype of a "soft" technology.

The types and number of industrial processes using enzymes are still limited. However, they are expected to grow. (See Ullmanns Enzyklopädie der technischen Chemie, vol. 10, pp. 522-526 ff., Verlag Chemie, 1975, and Kirk-Othmer, Encyclopedia of Chemical Technology, 3rd ed., vol. 9, pp. 73-224, John Wiley & Sons, 1980.)

Such processes are employed particularly in food and feedstuff technology, in detergent technology and in the manufacture of leather, where the use of enzymes has long been a tradition. Enzymes are also used in selective chemical reactions. (See Raul Präwe, Jahrbuch Biotechnologie, 1986-87, pp. 359-397, Carl Hanser Verlag, Munich.) Important examples, of industrial enzymes (IE) are gamma-aminobutyrotransaminase, amylase, cellulase, collagenase, glucose oxidase, glutamic acid decarboxylase, hemicellulase, invertase, catalase, lipase, pectinase, penicillase, protease, and streptokinase, among others.

The media in which the enzymes occurring in nature are active are predominantly aqueous media, where a certain dependence on the pH value and on the dissolved constituents of the aqueous medium is frequently observed, and the aqueous medium may therefore be regarded as the standard medium in enzymatic reactions.

Since enzymes are polypeptides whose activity depends primarily on their structural organization and which, like other proteins, can also be denatured by certain organic solvents, caution has always been indicated in the use of organic solvents together with enzymes.

In the recent past, the effect of additions of water-soluble organic solvents to an aqueous medium has been determined, for example, in the course of investigations of immobilized enzymes, and it has been observed that as the dielectric constant decreases, the reaction rate increases. (See H. Weetall and P. Vann in Enzyme Engineering, vol 4 [ed., G. B. Brown et al.]; NCI Monograph No. 27 [ed., M. P. Stulberg], 1967, pp. 141-152.)

THE OBJECT

In handling chemical agents, and especially in proportioning them, it is often considered an advantage when they are present in liquid form. As a rule, incorporating liquid preparations into liquid reaction media entails fewer problems than admixing powders or other solids. This is true also of enzyme preparations.

This preference for working with liquid preparations can be observed in the detergent industry, for example. On the other hand, liquid enzyme preparations in particular pose many problems. The most important of these has to do with the the stability of such enzyme preparations. As mentioned above, enzymes in an aqueous medium are subject to the influence of other constituents of the medium, such as acids, bases, salts, surface-active and complexing components, other macromolecules, and particularly other enzymes, the substrates on which the enzymes act, and so forth.

Such additives may have either a stabilizing or a destabilizing effect. As stabilizing additives for certain enzymes in aqueous solutions, glycols, polyglycols, surfactants, proteins and protein hydrolyzates, synthetic polymers, carboxylic acids, specific cations or anions and the like have been proposed, for example. (See U.S. Pat. No. 4,519,934; L. Kravetz and K. F. Guin, Journal of the Am. Oil Chem. Soc., vol. 62, 5, [1985]; L. Gianfreda, M. Modafferri and G. Greco, Enzyme Microb. Technol. 7, 78-82, [1985]; K. Martinek and V. P. Torchilin, Enzyme Microb. Technol. 1, 74-82 [1979]; U.S. Pat. Nos. 4,111,855 [1978], 4,318,818 [1982], 3,557,002 [1971] and 4,169,817 [1979].)

The formation of inverse micelles in a water/surfactant/organic solvent system has been taken into consideration as a further possible approach to the stabilization of enzymes in aqueous solution. See P. L. Luisi, Angew. Chemie 97, 449-460, [1985].)

The object of the present invention will now be explained in greater detail with reference to enzymes or enzyme systems used in the manufacture of leather.

Liquid proportioning has gained much ground of late over solids proportioning especially in leather manufacture since it does indeed offer advantages with regard to handling, for example. However, the preparation of liquid preparations containing enzymes, such as enzymatic bating and soaking aids, poses the problem of insufficient stability of these products. This instability, particularly of pancreatic preparations, is by no means an unexpected development but is already known to some extent from enzyme processing, In the case of proteases, allowance must also be made for the self-digesting action in particular and for the decomposing effect on other enzymatic proteins which are present. (See K. Martinek and V. P. Torchilin, Enzyme Microb. Technol., vol. 1, pp. 74-82 [1979].)

It should be noted that liquid enzyme preparations have failed so far to gain commercial acceptance. Thus there has been a continuing need for liquid enzyme formulations (a) which are stable under the conditions of use, (b) in which the activity of the enzymes preferably is not affected or not irreversibly affected, (c) which are compatible with the intended end-use areas of the enzymes, and (d) which are economically and ecologically acceptable. To be suitable for use with modern leathermaking methods, the loss of activity of such a so-called liquid enzyme should not exceed 15 percent over a period of from four to six months.

THE INVENTION

It has now been found that the inventive liquid enzyme formulations surprisingly meet practical requirements to a high degree. The invention relates to liquid enzyme formulations for technical use wherein the vehicle for the enzymes is at least one substantially anhydrous organic liquid or a mixture of such liquids. Suitable liquids for this purpose are liquids which are consonant with the above requirements, are advantageously in common use, and preferably are ecologically safe and in particular substantially nontoxic and noninjurious to enzymes. The organic liquids to be used in accordance with the invention are preferably hydrocarbons, but may contain oxygen or, less preferably, sulfur. Liquids of the formula (I)

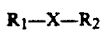

are preferred, wherein, when X is carbonyl, $R_1$ and $R_2$ are the same or different alkyl having 1 to 3 carbon atoms. If X is COO, then $R_1$ and $R_2$ are the same or different alkyl having 1 to 6 carbon atoms or $R_1$ is hydrogen and $R_2$ is such alkyl. If X is oxygen or sulfur, $R_2$ is hydrogen or alkyl having 1 to 8 carbon atoms and $R_1$ may be alkyl having 1 to 8 carbon atoms, or is

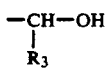

in which $R_3$ is hydrogen, $-CH_3$ or $-CH_2OH$, or $R_1$ is $-(CH_2-CH_2O)_n-H$, where n is an integer from 1 to 15.

$R_1$ and $R_2$ may also each be $-CH_2-CH_2OH$.

Further, $R_1$ and $R_2$, taken together with an oxygen or sulfur atom therebetween, may form a 5- or 6- membered ring in which all ring members are $-CH_2-$, except that one such ring member may be carbonyl (C=O) and one further such ring member may be oxygen.

Additional liquids include those of the formula (II)

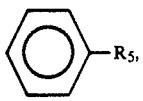

wherein $R_5$ is $-CH_3$ or $-CH=CH_2$.

Illustrative of liquids of formula (I) are particularly carbonic esters, and more particularly cyclic carbonic esters such as ethylene carbonate and, specifically, propylene carbonate. Also of interest are polyhydric alcohols such as glycerol, ethylene glycol, butyl glycol, butyl diglycol, diethylene glycol, polyethylene glycols (MW at least 400), liquid polypropylene glycols, and etherified derivatives thereof; monovalent alcohols or fatty alcohols such as methanol, ethanol, isopropanol, n-butanol, isobutanol, 2-ethyl hexanol, and cyclohexanol; ethers such as diethylether, methoxypropanol, diethylene glycol monomethyl ether, and particularly cyclic ethers such as dioxan and tetrahydrofuran; ketones such as acetone, ethylmethyl ketone, and cyclohexanone; esters such as ethyl acetate and butyl acetate; and lactones such as F-butyrolactone. Also to be mentioned are oxoalcohols and their ethoxylation products having 3 to about 14 ethylene oxide units; fatty alcohols and their ethoxylation products; olefins and their sulfonated derivatives such as $C_9-C_{12}$-a-olefin sulfonate, for example in the form of the sodium salt; and fatty alcohol ether sulfates such as sulfated $C_{12}-C_{15}$-alcohols, condensed with ethylene oxide.

Further liquids are fatty acid alkanolamides, such as $C_{16}-C_{18}$-fatty acid ethanolamide; and alkylphenol compounds such as octylphenol and ethoxylated derivatives thereof, such as nonylphenol ethoxylate with 8-9 moles of ethylene oxide.

Further, mixtures of organic liquids can be of advantage.

Representatives of liquids of formula II are toluene and styrene. Also, turpentine, solvent naphtha, white spirit, aliphatic hydrocarbons, and petroleum oils (boiling point range preferably between 50° C. and 180° C., and especially between 70° C. and 150° C.) are useful. With the exception of the polyethylene glycols, as a rule these are liquids having a molecular weight less than 110 and for the most part having a boiling point below 300° C. at normal pressure. (Further information concerning suitable liquids can be found in the monograph of Gnamm and Fuchs, Lösungsmittel und Weichmachungsmittel [Solvents and Plasticizers], 8th edition, Wissenschaftliche Gesellschaft, Stuttgart, 1980).

The organic liquids to be used according to the invention are essentially anhydrous, i.e. as a rule they contain less than 1 percent by weight of water, and preferably not more than the usual mechanically held moisture. Drying of the liquids is carried out conventionally, for example by means of commonly used desiccants distillation, including azeotropic distillation, etc. (See Houben-Weyl, vol. I/2, pp. 765-886, Georg Thieme Verlag, 1959).

The presence of water in the preparations of the invention generally is not contemplated, at least not in amounts that would be detrimental to the purposes of invention. When liquids are used which do not mix with water, the enzyme formulations may further contain surfactants. Preferred are nonionic surfactants of the type of the fatty alcohol/alkyl phenol ethoxylates (with oleocetyl-and olein-alcohol, for example); moreover, adducts of polyglycols with from 4 to 42 moles of ethylene oxide, apart from anionic types such as alkyl sulfates, alkyl ether sulfates, alkyl phosphates, alkyl ether phosphates, alkyl sulfonates and alkylaryl sulfonates. (See German patent 33 22 840.) The amount of the surfactants generally ranges from 0.001 to 50 weight percent, and preferably from 0.005 to 20 weight percent, based on the liquid vehicle. The hydrophile-lipophile balance (HLB) of the emulsifiers (or the o/w emulsifying action) generally ranges from 8 to 18, and preferably from 9 to 15. (With respect to emulsifiers and HLB, see Kirk-Othmer, 3rd ed., vol. 8, 910-916.) Also preferred are liquids which do mix with water, and especially liquids which are miscible with water in any ratio. On first approximation, it should be assumed that the enzymes remain completely undissolved in the liquids. The tendency to self-digestion or to decomposition of other enzymes thus is greatly minimized.

The quantity of the liquids used is based mainly on practicality in the handling of the enzymes and is not really critical. In general, the weight ratio of enzyme to liquid will not be less than 1:10, for reasons of handling ease. For the sake of reasonable concentrations, the upper limit of the weight ratio of enzyme to liquid will generally range from 1:30 to 1:500. As a rule of thumb, a ratio of enzyme to liquid of from 1 to about 50 has proved practical. Optionally, mixtures of the liquids recited above may be used. As the enzymes, which are essentially proteins, are added to the substantially anhydrous liquids, problems such as slow wetting and/or dispersal problems such as settling or creaming may arise.

In developing the present invention further, it was found that the problems arising in the preparation of homogeneous liquid enzyme formulations, such as creaming and settling, can be solved at least in part by dispersing inorganic powdered additives in the liquids.

Powdered additions of inorganic dispersants have been described for altogether different applications, namely, as dispersants for oil-in-water emulsions or as dispersants in free-radical bead polymerization. (See Houben-Weyl, Methoden der organischen Chemie, vol. XIV/1, Macromolecular Substances, pp. 420–421, Georg Thieme Verlag, 1961.) For example, insoluble salts of the alkaline-earth metals (carbonates, phosphates, sulfates and silicates), aluminum hydroxide, talc, bentonite, and, particularly, silicon dioxide, and especially pyrogenic silicon dioxide (fumed silica). (See Kirk-Othmer, op. cit., vol. 20, pp. 748–781; Ullmanns Encyclopädie der Technischen Chemie, 4th edition, vol. 18, pp. 652–656, Verlag Chemie 1979.)

The pyrogenic modifications of silicon dioxide are known to be prepared by gas-phase reactions, for example by flame hydrolysis or by use of an electric arc. They generally consist of spherical particles having a primary particle size from 5 to 500 nanometers. Their density is about 2.2 g/cm$^3$. Such materials are available commercially under the names "Aerosil" and "Cab-o-Sil".

Additionally, clays, particularly bentonite, are suitable for the aforementioned purpose, although attention must be paid that certain enzymes, for example pectinases, are adsorbed on bentonite with loss of activity.

Kaolin and bentonite are known to form thixotropic gels with a number of polar and nonpolar organic liquids. The thixotropy of the gels disappears upon the addition of minor amounts of longer-chain alcohols, for example. (See Ullmanns Enzyklopädie der technischen Chemie, 4th ed., vol. 23, pp. 318–326, Verlag Chemie, and U. Hoffmann et al., Kolloid-Z. 151, 97–115 [1957].)

By clays are meant the usual aluminosilicates, and by bentonites the commercial preparations consisting mainly of montmorillonite ($Al_2O_3 \cdot 4SiO_2 \cdot H_2O$). Of special interest are organically activated bentonites, for example, those formed by reaction of sodium montmorillonite with quaternary alkylammonium compounds. Through cation exchange, so-called organophilic bentonites, which swell in organic liquids, are formed. (See Ullmanns, loc. cit., p. 323.) As a rule, the commercial grades (flakes, particle sizes ranging from 0.5 to 5 microns) may be used. However, it is advisable to subject them to a treatment with shearing action in the liquid selected. As a rule, the liquids should contain from 0.1 to 3 weight percent, and preferably from 0.3 to 1 weight percent, based on the liquid, of inorganic additives. It has proved particularly advantageous to subject the inorganic addition to the enzyme concentrate, together with the liquid, to shearing action in appropriate equipment, and particularly in a dispersion mill. The latter may be of the commercial type. (See Ullmanns Enzyklopädie der technischen Chemie, 4th ed., vol. 1, p. 239, Verlag Chemie, 1972.)

The rotational speed and the treating time depend mainly on the type of the equipment. A treating time of from 2 to 60 minutes at a peripheral speed of from 4 to 36 meters per second will serve as a guide for the action of commercial dispersing apparatus on bentonite in one of the liquids to be used in accordance with the invention.

Propylene carbonate has been found to be a particularly effective liquid, especially in combination with silicon dioxide or with bentonite.

So far as is known, the formulations of the invention are not subject to any restrictions with respect to the enzyme component, except insofar as the stability of the enzymes themselves to organic liquids such as alcohols is concerned. A requirement is that the organic liquid vehicle must be compatible with the end use of the enzymes. It was not to be foreseen that, by the use of inorganic dispersing agents, organic liquid carrier systems for enzymes could be prepared, which systems would in general more closely approach the ideal requirements of technology, not only from the viewpoint of physical and biological stability, but also from the point of view of ready availability.

To enchance the anti-settling or anti-creaming effect, weakly polar organic liquids may be added to the vehicles, especially when the latter are polar liquids of the type of formula (I). Thus, it may be advantageous if the vehicle contains from 1 to 10 percent by weight of hydrocarbons, and particularly branched or linear aliphatics having from 5 to 20 carbon atoms. Illustrative of these are petroleum fractions in the boiling range of approximately 50° to 180° C. See also the above definition of liquid.

The enzymes are primarily those which are already being used industrially or in other fields of application. (See "The Prior Art" above.)

(A) Proteases (EC 3.4; Kirk-Othmer, loc. cit., vol. 9; Aunstrup in "Industrial Aspects of Biochemistry" (B. Spencer, ed.), vol. 30 (I), pp. 23–46, North Holland, 1974).
 (a) animal-derived, for example:
  ($a_1$) Rennin (EC 3.4.23.4.)
  ($b_2$) Pancreatic proteases:
   Pancreatin, and particularly trypsin and chymotrypsin (optimum pH range about 7 to 10);
   Pepsin (EC 3.4.23.1) (optimum pH range about 1.5 to 4.0;
   Cathepsin (EC 3.4.23.5) (optimum pH range about 4.0 to 5.0).
 (b) Plant-derived:
  ($b_1$) Papain (EC 3.4.22.1) (optimum pH range about 5.0 to 8.0);
  ($B_2$) Ficin (EC 3.4.22.3) (optimum pH range about 4.0 to 9.0);
  ($b_3$) Bromelain (EC 3.4.22.4 and 3.4.22.5) (optimum pH range about 5.0 to 7.0.
 (c) Microbially derived (see L. Keay in "Process Biochemistry", 1971, 17–21):
  ($c_1$) From *bacillus* species, for example, *B. subtilis, B. licheniformis, B. alkalophilus, B. cereus, B. natto, B. vulgatus, B. mycoides.*
  ($c_2$) From *streptococci.*
  ($c_3$) From *streptomyces*, for example, *Streptomyces fradiae, S. griseus, S. rectus.*
  ($c_4$) From *aspergillus* species, for example, *Aspergillus flavus-oryzae, A. niger, A. saitoi, A. usamii.*
  ($c_5$) From members of the genera *Mucor* and *Rhizopus*, for example, *Mucor pusillus, M. mietrei.*
  ($c_6$) From *endothia* strains, for example, *E. parasitica.*
  ($c_7$) From *trametes* strains, for example, *Trametes sanguinea.*

Enzymes are classified not only according to their source but also on the basis of the site of attack (exoenzymes vs. endoenzymes) and of the active site of the proteases (serine proteases, which are inhibited by diisopropyl fluorophosphate [DFP]; sulfhydril enzymes).

A factor that is of considerable practical importance is that enzyme activity is a function of pH.

From a practical point of view, proteases are therefore classed as follows:
 (i) Alkaline proteases with optimum activity in the pH range of about 7.5 to 13, and particularly alkaline bacterial proteases (EC 3.4.21), most of which are of the serine type, and alkaline fungal proteases.

(ii) Neutral proteases with optimum activity in the pH range from 6.0 to 9.0, and particularly neutral bacterial proteases (EC 3.4.24), which belong to the metalloenzymes, and fungal proteases such as bacillus proteases, pseudomonas proteases, streptomyces proteases, and aspergillus proteases.

(iii) Acid proteases with optimum activity in the pH range from 2.0 to 5.0 (EC 3.4.23), and particularly acidic fungal proteases, for example, from Rhizopus species, Aspergillus species, Penicillium species, *Mucor* species, as well as *Impex lacteus* and *Endothitia parasitica*.

Proteases are used industrially in leather manufacture, in detergents and in cleansing, in desizing, in cheesemaking, in the tenderization of meats and in the stabilization of beer, for example.

Examples of alkaline proteases are, in particular, the subtilisins, alkaline bacterial proteinases of the serine type, which in the pH range from 9 to 10 are stable and relatively insensitive to perborate.

The proteolytic activity of enzymes is usually determined by the Anson hemoglobin method (M. L. Anson, J. Gen. Physiol. 22, 79 [1939 or by the Löhlein-Volhard method ("Die Löhlein-Volhard'sche Methode zur Bestimmung der proteolytischen Aktivität" in Gerbereichemisches Taschenbuch, Dresden/Leipzig, 1955) and in that case expressed in LVU (Löhlein-Volhard units).

An LVU is the amount of enzyme which under the specific conditions of the method digests 1.725 mg of casein. For determination of the activity of enzymes active in the acid range, units are also used in what follows which are derived from the Anson method. These units are known as "proteinase units (hemoglobin)", or $U_{Hb}$. One $U_{Hb}$ corresponds to the amount of enzyme which catalyzes the release of fragments soluble in trichloroacetic acid from hemoglobin equivalent to one micromole of tyrosine per minute at 37° C. (measured at 280 nm). (1 $mU_{Hb} = 10^{-3} U_{Hb}$.)

(B) Amylases (EC 3.2; see Ullmanns, loc. cit., vol. 10, pp. 506–510, and "Industrial Aspects of Biochemistry" (B. Spencer, ed.), loc. cit., pp. 143–144, 175).

(a) Endoamylases:
   ($a_1$) alpha-Amylases (alpha-1,4-glucosan hydrolases) (EC 3.2.1.1)
   ($a_2$) alpha-1,6-glucosan hydrolases
Exoamylases (saccharogenic amylases):
   ($b_1$) beta-Amylases (alpha-1,4-glucosanmaltohydrolases) (EC 3.2.1.2)
   ($b_2$) Glucoamylases (alpha-1,4-glucosanglucohydrolases) (EC 3.2.1.3)

Alpha-amylases are known to occur in plants, for example, together with beta-amylases. They are commercially produced from pancreas and from bacterial and fungal cultures.

They are obtained most readily from *bacillus* species such as *B. subtilis, B. mesentericus, B. polymixa, B. amyloliquefaciens* and *B. licheniformis*; from fungi, and particularly from *aspergillus* species such as *A. niger, A. phoenicis, A. oryzae* and *A. awamori*; from *Mucor* strains such as *M. rouxianus*; from *Rhizopus* strains such as *R. delemar, R. oryzae* and *R. japonicus*; and from *endomyces* strains such as *E. fibuliger*. The pH optimum of alphaamylases is predominantly in the range from 4.7 to 7.2. Amylases find use in the food industry (see "Biotechnology" H.-J. Rehm & G. Reed, ed., vol. 5, Verlag Chemie, 1983; "Industrial Aspects of Biochemistry"[B. Spencer, ed.], vol. 30, part I, pp. 139–186 and 213–260, Elsevier [1973]), in the liquefaction of starch, in malt production, in the production of ethanol, in desizing, in leather manufacture, etc.

The activity of alpha-amylases can be determined, when starch is used as the substrate, by the method of Sandstedt, Kneen & Blish (Cereal Chem. 16, 172 [1939] and Technical Bulletin No. 1024, U. S. Department of Agriculture). One amylase unit (=one SKB unit) is the amount of enzyme which at 30° C. and under the other conditions specified is able to dextrinate one gram of soluble starch in one hour.

The Willstätter method is used to determine the activity of pancreatic amylase. (Hoppe-Seylers, Z. physiol. Chem. 126, 143 [1923].) A Willstätter amylase unit is defined as 100 times the amount of enzyme which under the test conditions specified breaks down starch at such a rate that the monomolecular reaction constant is 0.01.

(C) Lipases (EC 3.1.1.3)

As is known, lipases are carboxyl esterases which cleave glycerol ester in aqueous emulsion. Thus they differ from other carboxyl esterases which attack the substrate in aqueous solution. p (a) Pancreatic lipases The pancreatic enzyme complex contains, apart from lipases, mostly esterases as well as proteases and amylases as commercially important companion enzymes. The pH optimum (for olive oil) is in the range from 7 to 8.5, with the range of activity extending from pH 6.5 to 9.5.

Lipases are generally highly-unstable, especially to proteolytic breakdown by companion proteases.

(b) Microbiological lipases, for example, from *Pseudomonas fragii, Aspergillus* species (e.g., *A. luchuensis, Candida cylindracea, Geotrichum candidum, Humicola lanuginosa, Mucor pusillum, Penicillium* species (e.g., *P. chrysogenum, P. oxalicum*), and *Rhizopus* species (*R. nigricans, R. oryzea*).

These lipases generally have at least one pH optimum at a pH above 7.0. To the extent that their instability permits it, lipases find use in waste disposal, in leather manufacture and in the food industry, for example.

(D) Catalases/hydroperoxidases (EC 1.11.1.6):
   (a) From animal tissue, for example, from liver.
   (b) From plants, for example, from horseradish.
   (c) From microorganisms, for example, from *Micrococcus lysodeicticus*.

Catalases are used in peroxide bleaching and in the milk industry.

(E) Cellulases (EC 3.2.1.4) See Ullmanns, loc. cit., pp. 510–511.)

As is known, cellulase is an enzyme complex whose components successively take part in the breakdown of native cellulose.

Cellulases are found in insects, mollusks and microorganisms (bacteria, mold fungi). Commercially utilized sources of cellulases are particularly aspergillus, neurospora, rhizopus, trichoderma and trametes strains.

Commercial preparations have optimum activity between pH 4 and 6. Prior-art cellulase preparations lose approximately 10 to 20 percent of their activity per year.

Cellulases find commercial use in the food industry for conversion of cellulose-containing wastes, etc. The present invention will now be described in greater detail with reference to the use of enzymes in the manufacture of leather. The use of enzymes, and particularly of proteolytic enzymes, has been part and parcel of leathermaking, and particularly of the beamhouse processes, since the introduction of the enzymatic bate and tryptic digestive enzymes from the pancreas in the "Oropon ®" bate by Dr. Otto Röhm (German patent 20 05 19) some 80 years ago.

In addition to being used in bating (German patents 9 27 464, 9 76 107, 9 41 811, 9 74 813, 9 75 095, 9 76 928, 11 20 066, 11 34 474, 12 19 620 and 12 82 837 and U.S. Pat. Nos. 3,939,040 and 4,273,876, enzyme preparations are used also in soaking (German patents 2 88 095, 9 76 602, 10 22 748, 10 34 317, 12 82 838 and 20 59 453, and U.S. Pat. No. 4,278,432 and 4,344,762); in hair loosening and opening up (U.S. Pat. No. 4,294,087); in unhairing (German patents 10 26 038, 12 11 349, 11 55 560, 12 30 169 and 12 88 728, and U.S. Pat. No. 3,623,950); in liming German patents 10 23 183, 12 03 416, 20 53 016 and published German patent application OS 34 29 047); in pickling (German patents 8 47 947 and 9 41 680) or in a compact process (U.S. Pat. Nos. 3,986,926 and 3,966,551); in wet degreasing (German patent 33 12 840); for loosening the fibrous structure of furs (U.S. Pat. Nos. 3,549,495 and 3,558,430), etc. Enzyme preparations are further used to dissolve untanned machine trimmings and other byproducts of leather manufacture (U.S. Pat. No. 4,210,721, Swiss patent 631,486, U.S. Pat. Nos. 4,293,647 and 4,220,723), keratin-containing raw stock (U.S. Pat. No. 4,232,123), elastin-containing preparations (U.S. Pat. No. 4,179,333); for working up collagen-containing raw stock (U.S. Pat. No. 4,220,714), etc.

Consistent with the aforesaid enzymatic processes, liquid enzyme formulations in accordance with the present claims may be used in the various operations of leather manufacture (see Ullmanns Enzyklopädie der technischen Chemie, 3rd ed., vol. 11, p. 609, Urban/Schwarzenberg; Ullmanns Enzyklopädie der technischen Chemie, 4th ed., vol. 16, pp. 111–174, Verlag Chemie, 1978; F. Stather, Gerbereichemie und Gerbereitechnologie, 4th ed., Akademie-Verlag, Berlin, 1967), namely:

(I) in soaking,
(II) in hair loosening, liming and unhairing,
(III) in deliming and bating, and optionally
(IV) in pickling. Usually the liquors are in the range of from 50 to 500 weight percent based on the weight of the hides and skins used in the respective steps.

(I) Soaking

The soaking of hide stock, in which the hardening of the, hides, or skins, resulting from salt curing is reversed, is usually carried out at a pH between 7.0 and 10.0. The concurrent use of enzymes, and particularly of proteolytic enzymes (see [A] above), accelerates the softening action through "digestion" of the water-soluble and other albumins which are not a part of the collagenous fiber structure of the hide.

In general, enzymes whose range of activity (or pH optimum of the proteolytic activity) falls between pH 7.00 and 10.0 are employed in soaking. Removal of the noncollagenous albumins assures faster and more intensive wetting of the hide.

The soak water is advantageously made slightly alkaline; however, the pH value should always remain below 12. The use of soaking aids (such as monoethanolamine with an antiseptic such as zephyrol or naphthalenesulfonic acid in combination with substituted phenols; highly sulfonated ricinoleic acid butyl ester with a methylcyclohexanol mixture fatty alkyl sulfates with solvents) is also advantageous. Examples of suitable enzymatic additives for the inventive liquid enzyme formulations are the proteases listed under (A) above, and particularly those named under (A) (c), and more particularly microbial proteases active in the pH range from 4 to 9.5, especially fungal proteinases from *aspergillus* species such as *A. saitoi* and *A. usamii*, for example, and particularly acid proteinases with activity in the pH range from 2.5 to 4.5; also those from *A. oryzae* active in the pH range from 4.0 to 9.5, and those from *A. niger* and *A. flavus* active in the pH range from 9.5 to 11.0.

The concentration of proteolytic activities of the proteinases used generally ranges from 0.1 to 1.0 Anson units, or from 1,000 to 3,000 LVU, per liter of soak liquor.

The soak liquors may, further contain amylases according to (B) above. Amylases occur as companion enzymes of fungal proteinases. They promote the cleavage of glucosidic bonds in the proteoglycans and glycoproteins of the hide.

Well suited are amylases of microbial origin, and more particularly those from aspergillus species such as *A. oryzae* and *A. niger*, especially those active in the pH range from 3.0 to 5.8. Suited for use are also those of bacterial origin, for example, those derived from *Bacillus subtilis*, *B. mesentericus* and *B. polymixa* with activity in the pH range from 5.0 to 7.0.

As a rule, the glycolytic activity of amylases ranges from 500 to 2,000 SKB.

The temperature of the soak liquors is advantageously higher than 20° C. The soaking duration should be as short as possible and generally is between 4 and 36 hours.

(II) Hair loosening, liming, opening up

For unhairing, lime liquors are used most often. (See Ullmanns, loc. cit., 3rd ed., vol. 11, p. 560; 4th ed., vol. 16, pp. 118–119. So-called sharpened lime liquors, preferably a combination of calcium hydroxide and sodium sulfide, are used throughout and in the presence of buffering, swelling-inhibiting liming aids such as wetting agents, and particularly cationic wetting agents, in combination with monoethanolamine and disinfectants, for example, quaternary alkyldimethylbenzylammonium compounds, or dialkylamine and its sulfate. For hair loosening and opening up, enzymes which in this pH range remain sufficiently stable may be used in addition to the usual liming chemicals. Soaking and liming may be combined by gradually increasing the pH value and using appropriate enzymes.

The use of enzymes in conjunction with the liming-/hair loosening/unhairing operations generally takes place in the pH range from 9 to 11, and more particularly from 9 to 12.

Consistent with German patent 29 17 376 or U.S. Pat. No. 4,294,687, respectively, the hide, freed of curing salt, may first be pretreated in the acid pH range with substances cleaving disulfide bridges, and then hair loosening and opening up may be brought about simultaneously without prior soaking by the use of proteases active in the alkaline range at a pH of about 11 to 13. This is then followed by the further processing steps (III) and optionally (IV) usually carried out in the beamhouse. It is advisable to use in the beamhouse operations (II) alkaline bacterial proteinases (serine proteases), for example, from *B. subtilis*, *B. licheniformis*, *B. firmus*, *B. alcalophilus*, *B. polymixa* and *B. mesentericus*.

These proteases generally have an activity ranging from 8,000 to 10,000 LVU per gram. They are advantageously used in amounts of from 0.1 to 10 weight percent, and preferably from 1 to 5 weight percent, based on the weight of the salted hides and skins (raw weight).

The enzymatic reaction in unhairing and opening up is carried out at about 18 to 28° C. The reaction time generally ranges from 12 to 24 hours, and more particularly from 12 to 16 hours.

Unhairing or dewooling can also be performed with alkaline fungal proteinases of the above type (i), for example, with aspergillus proteases, and particularly with those from *A. niger* and *A. flavus* which are active in the pH 9.5 to 11.0 range.

Moreover, the enzymatic unhairing method of German patent 34 29 047, in which hides and skins are treated in a liquor in the pH range from 9 to 11 with proteolytic enzymes having optimum activity in the pH range from 2 to 7.5, may be employed, unhairing being then carried out. The enzymes used then are proteases of the above type (iii), and particularly from *A. oryzea, A. saitoi, A. parasiticus, A. usamii* and *A. awamori*, from *Paelomyces* species, *Penicillium* species or also *Rhizopus* species and/or from *Mucor pusillus* as well as the acid proteases listed under (A) (a) and (A) (b) above.

As a rule, from 0.5 to 6 weight percent, and preferably from 1 to 3 weight percent, based on the weight of the salted hides or skins, is used. The activity generally ranges from 50 to 200 $mU_{Hb}$.

(III)

Deliming and bating are preferably carried out with the aid of enzymes. Deliming serves to reduce the alkalinity of the pelts from a pH value between 13 and 14 to a pH of from 7 to 8. Deliming is preferably done, not with strongly dissociated but with weak organic acids of the type of the dicarboxylic acids, Or then with weakly acid salts. In bating, residues of epidermis, hair and pigments should be removed and further opening up should be brought about. Moreover, noncollagenous albumin constituents should be removed. (See Ullmanns, 4th ed., vol. 16, loc. cit., pp. 119-120.) Bating is carried out conventionally at pH 7.5 to 8.5. The use of cyclic carbonates in deliming is known from German patent 31 08 428.

The duration of the bate as a rule is between 1 and 6 hours, preferably 1-2 hours as a short bate. As a rule of thumb, the proteases can be used in such amount that from 1 to 10 Löhlein-Volhard units are present per gram of pelt weight.

The temperature is advantageously between 25° C. and 35° C., preferably 30° C. Any conventional commercial tanning vessel, such as a drum, paddle-vat, mixer, or tanning machine can be used (See O'Flaherty et al., *The Chemistry and Technology of Leather*, vol. 1, ACS Monograph Series, Reinhold Publishing Corporation, New York 1956).

Lipases according to (C) above, for example, pancreatic lipases exhibiting activity in the pH 7.0 to 9.0 range, may be used concurrently in bating.

Amylases according to (B) above, for example, pancreatic amylases which are active at a pH of from 5.5 to 8.5 and promote the cleavage of glycoside linkages in bating, will also exert a beneficial influence on bating, particularly as companion enzymes of trypsin and chymotrypsin.

(IV) Pickling

To prepare the pelt for mineral tanning, it has to be acidified, that is, its pH has to be reduced from about 8 to the 3 to 4 range. This is done in the pickle liquor, which is an acid/salt solution in water, for example, sulfuric acid or formic acid together with sodium chloride.

Recommended are mold tryptases, pancreatic tryptases and bacterial tryptases, for example, optionally together with carbohydrate-splitting enzymes, derived in particular from bacteria or from mold fungi.

ADVANTAGES

The inventive liquid enzyme formulations offer a generally applicable solution, not likely to give rise to difficulties, to the problem of making use of liquid enzyme formulations, which is often desirable. Being able to combine enzymes with other components which in an aqueous medium and on prolonged exposure would interfere with enzyme activity is a further advantage. This is true particularly of the ability to combine different enzymes, for example, proteases, not only with amylases, lipases, etc., but also with hydrotropes such as urea, guanidine salts, cumene sulfonate, etc.

More in particular, the following advantages of the liquid preparations of the invention over powdered preparations are evident:

Economic advantages: water soluble salts such as ammonium sulfate or sodium sulfate which are commonly added to powdered enzymes as diluents and/or stabilizers can be dispensed with in the preparations of the invention. Nonliquid components amount to only a fraction of those present in conventional preparations. The salt content of prior art products, further, is responsible for a number of leather imperfections which, thus, can be avoided using the new preparations.

Ecological advantages: the loading of waste water with salts and the like, which represents a considerable source of pollution, for the most part disappears. As surface active agents, biologically degradeable agents are preferably employed.

Greater applicability: The invention permits the combination of enzymes with one another, with further treating agents, with activators, and the like, which are incompatible in aqueous concentrates. In contrast to aqueous enzyme preparations, the enzyme concentration in the preparations of the invention can extend over a wide range.

Extreme stability: to the limit of current experience, the preparations of the invention are very stable. For instance, a combination of fungus proteases and pancreatic enzymes is still stable after 6 months' storage. The danger of contamination, for instance with microorganisms, is minimized. The need for anti-fungal or anti-bacterial protection is unnecessary. In aqueous liquid enzyme preparations, the stabilizing agents which are employed adversely affect enzyme activity.

Uniform enzyme activity: experience, especially in the area of conventional leather preparation, has shown that the use of enzymes leads to defects in the product if the enzyme activity is non-uniform, as, for example, in the use of solid enzyme preparations. The liquid preparations of the invention can be dispersed more uniformly and more rapidly.

Safety considerations: in contrast to powdered preparations, the liquid formulations of the inventions are far superior from the point of view of safety, since there is no development of dust and no provocation of allergies. In comparison with aqueous preparations, there is the advantage that in case of spills, leaks, splashes, and other such accidental loss of the enzyme preparation, the enzyme is not immediately active but, as a rule, becomes so only upon the addition of water.

Dosing advantages: because of the stability of the enzyme in an organic medium, constant enzyme activity can be assumed. Hence, measurement of the preparation with the necessary accuracy can be by volume, eliminating the need for inconvenient weighings in order to establish the required enzyme concentration.

Compatibility with auxiliaries: auxiliaries desired in the final product, such as builders, polyphosphates, or zeolites, can be dispersed in the liquid organic carrier together with the enzyme, which is not possible using an aqueous phase.

Stability to creaming and settling: in contrast to enzyme preparations in which, for example, a crystalline enzyme is preserved in an organic liquid such as toluene, whereby the enzyme, for example a pancreatic enzyme, usually settles on the floor of the container, the invention makes available stable enzyme dispersions in which the stabilizer in no way adversely affects the enzyme activity. In contrast, the stabilizer in aqueous liquid formulations as a rule considerably degrades enzyme activity.

The examples which follow will serve to elucidate the liquid enzyme formulations of the invention and their use. An asterisk at the solvent shall indicate, that it is miscible with water at all proportions at room temperature.

EXAMPLES

EXAMPLE A

Preparation of a liquid enzyme preparation based on pancreatic and fungal enzymes 700 g of propylene carbonate (0.6% water) to which 3.5 g of an organically modified bentonite (e.g., "Bentone 27", marketed by Kronos Titan, Leverkusen) has been added are dispersed for 45 to 60 minutes at a rotative speed of 16 meters/second in a toothed-disk agitator. (Disk : tank = 1:2.5; the filling height is from 2 to 2½ times the disk diameter; the spacing of the agitator from the floor is one-half the disk diameter.)

With further dispersing, 2.54 g of a fungal protease concentrate derived from *Aspergillus parasiticus* (150,000 LVU; pH optimum, 7.5 to 9) and 1.48 g of a pancreatic enzyme preparation (220,000 LVU; pH optimum, 6 to 8) are added. Dispersing is then continued at constant rotative speed, care being taken to not exceed a temperature of 40° C. The end product has an activity of 1,000 LVU and exhibits no loss of activity after 4 weeks at 20° C. No creaming or settling of the enzyme is observed in the product.

The dispersing conditions (rotative speed) and the type of the organically modified bentonite have to be adjusted according to the type of the solvent, the particle size, and the concentration of the enzyme concentrate.

EXAMPLE B

Combined deliming and bating with a liquid enzyme product based on pancreatic and fungal enzymes in propylene carbonate 10 kg limed and washed bovine pelts; split thickness, 3 to 4 mm; 30% water; temperature, 35° C.; 3% enzyme solution comprising pancreatic and fungal enzymes in propylene carbonate as in Example A (activity, 1,000 LVU/g), 0.2% nonionic wetting agent based on fatty alcohol ethoxylate with from 8 to 9 moles of ethylene oxide.

After 80 minutes, the pelts are completely delimed throughout, and the scud is thoroughly loosened. The final pH of the liquor is 8.0. No toxic hydrogen sulfide escapes during deliming since the pH value never drops below 9.00.

EXAMPLE C 920 g of butyl glycol and 40 g of petroleum, boiling point 110 to 130, to which 30 g of an organically modified bentonite (e.g., "Bentone 27" of Kronos Titan, Leverkusen) has been added are dispersed for 38 minutes in an Ultra-Turrax agitator at 16 meters/second.

The dispersion is allowed to stand for 24 hours. Under the above dispersing conditions, 18.5 g of a neutral protease from a *Bacillus subtilis* strain (70,000 LVU/g; pH optimum, 5.5 to 7) is added. Dispersing is continued for another 5 minutes. The end product has an activity of 1,300 LVU. After 5 weeks, no loss of activity is evident from the LVU measurement. The liquid enzyme formulation remains homogeneous; there is no settling or creaming.

EXAMPLE D

Enzymatic soaking and degreasing of cattle hides soaked for dirt removal
Percentages based on salted weight:
100.0 kg cattle hides soaked for dirt removal
200.0% water at 26° C.
0.8% liquid enzyme formulation from Example C
0.4% nonionic wetting agent based on fatty alcohol ethoxylate with 6 moles of ethylene oxide
0.2% of a chloroacetamide-based bactericide After a soaking time of 5 hours, the hides have been completely soaked back and are at the same time ready for hair loosening. A large portion of the natural fat in the hides is emulsified in the soak liquor.

The hides soaked in the above manner are limed by prior-art methods and processed further into crust leather for shoes.

EXAMPLE E 1,000 g of petroleum, boiling point 110° to 130° C., is heated to 40° C. and after the addition of an organically modified bentonite (e.g., "MPA-X-2000" of Kronos Titan, Leverkusen) dispersed for 10 minutes. Then 2.5 g of an acid fungal protease from *Aspergillus parasiticus* (80,000 LVU/g; pH optimum, 3.5 to 5) are added and dispersing is continued for another 5 minutes.

A liquid enzyme formulation having an activity of 200 LVU is obtained which after 4 weeks at 20° C. exhibits no loss of activity. The solution is homogeneous and neither creams nor settles.

EXAMPLE F

Degreasing and enzymatic loosening of pickled sheep and lamb pelts
Drumming
(Percentages based on pickled weight)
200% of water at 35° C., 15% of sodium chloride, keep in motion for 5 minutes, add 10 kg of pickled pelts, and keep in motion for 30 minutes; flesh; drain liquor.
Degreasing
(Percentages based on fleshed weight)

30% of water at 35° C., 2% of a nonvolatile wetting agent based on fatty alcohol ethoxylate (6 to 8 moles of ethylene oxide), 6% of the liquid enzyme from Example E (200 LVU/g), 8 kg pickled pelts, keep in motion for 30 minutes.

The pelts are well degreased and loosened due to the action of the enzyme/surfactant/petroleum combination.

For depickling, commercial depickling tanning agents may be added to a replenished or fresh liquor and the stock may then be processed further conventionally.

EXAMPLE G 927.5 g of a non-ionic anhydrous wetting agent, prepared from nonyl phenol plus 8.5 mol of ethylene oxide and 12 g of fumed silica (Aerosil 380 ® product of Degussa, Hanau, West Germany) are mixed together with 5 g of a surface active agent (Borchigen STL ®, based on modified fatty acid, product of Borchers GmbH, Goslar, W.-Germany) in a stirring vessel. The mixture is dispersed for 15 minutes with a toothed-disk agitator at a rotative speed of 15–18 m/sec. The original viscosity of 15 mPas reaches 255 mPas, viscosity is determined using a Brookfield viscometer condition I/6 upm. With further dispersing 55 g of α-amylase 90 000 SKB/g (for SKB-units and analysis see R. M. E. Sandstedt, E. Kneen and M. J. Blish, Cereal Chem. 16, 712 (1939) Technical Bulletin No. 1024 U.S. Department of Agriculture) are added. After 15 minutes of further dispersing one obtains a liquid enzyme formulation with an initial activity of 5 000 SKB/g. No creaming or settling of the enzyme is observed after 4 weeks' storing in the product. The loss of activity after storage at 25° C. is 3.4%.

EXAMPLE H

Enzyme supported prewashing of jeans fabrics.

10 kg of denim cloth (jeans fabric) which had been sized with starch are put into 50 l of water at 40° C. to which 50 ml of the liquid enzyme formulation of example G are added in a washing machine. The temperature is then raised to 60° C. and the cloth is washed for 5–10 minutes and is twice rinsed afterwards with 50 l of water each time at 40° C.

An additional washing step using a wetting agent to dispose of degraded starch turned out to be not necessary. The cloth that has been desized in this way has a pleasant, soft feel.

EXAMPLE I

Liquid, biodegradable heavy-duty detergent 466 g of 1,2-propylene glycol * and 400 g of nonionic surfactant (Marlipal ® 013-90, isotridecyl alkohol plus 9 moles of ethylene oxide, product of Chemische Werke Hüls AG, W.-Germany), 100 g of ethyl alcohol (98%) plus 10 g of fumed silica (Aerosil 380 ®, product of Degussa AG, W.-Germany) and 4 g of a surface active agent (modified and etherified fatty acid Borchigen STL ®,product of Borchers GmbH, Goslar, W.-Germany) are mixed and dispersed in a stirring vessel using a toothed disk agitator for 15 minutes at a rotative speed of 15–18 m/sec. The viscosity of the liquid was found to be 1 250 mPas. The following components are added and are actively dispersed in the order 6 g of alkaline protease from Bacillus subtilis (activity 92 000 LVE/g)

4 g of amylase from B. subtilis (activity 90 000 SKB/g)

6 g of an optical brightener (4,4′-bis-(4-anilino-6-[N-(2-hydroxy ethyl)-N-(2-carbamoylethyl) -amino]-s-triazino-2-yl-amino-2,2′-stilbene-disulfonic acid 2 g of ethylene diamino tetraacetic acid, sodium salt (sodium salt of EDTA)

6 g of —$C_9$–$C_{12}$ olefinsulfonic acid, sodium salt (98%)

After addition of the components the mixture is exposed to dispersion conditions for another 15 minutes. A viscous yet readily pourable solution is obtained, which when stored for 4 weeks at 25° C. shows neither creaming nor settling. The α-amylase showed a loss of <1% of the original activity. The loss of activity of the protease was found to be 1.4%.

EXAMPLE J

Washing of a blood stained cotton fabric at 60° C. 500 g of a white cotton fabric which had been soaked with bovine blood and dried was treated with 6 g of the enzymatic detergent of Example I, (which had been stored for 3 month before use), in 2.5 l of water and 2 g of sodium metasilicate for 15 minutes at 60° C. Then the fabric was washed two times with 2.5 l of water at 30° C. For comparison the identical fabric stained in the same way was treated with 6 g of a liquid detergent which was identical to that of Example I, except that 1,2-propylene glycol had been replaced by water. Evaluation of the result of washing in both cases on the remission photometer ELREFOMAT DFC 5 ® (Zeiss, W.-Germany) showed that treatment with the anhydrous detergent preparation yielded a desorption of blood from the fabric that was 46% higher than with the aqueous preparation.

EXAMPLE K

Preparation of a liquid lipase preparation

In a vessel 968 g of a $C_{16}$–$C_{18}$ fatty alcohol reacted with 5 mol of ethylene oxide (Genopal 0-050 ®, product of Hoechst AG, West-Germany), 12 g of fumed silica (Aerosil 380 ®,product of Degussa AG, W.-Germany) and 4 g of a surface active agent (Borchigen STL ®,are dispersed by means of a toothed-disk agitator at a rotative speed of 15–18 m/s for 15 minutes. The viscosity of the system rises from 18 mPas to 290 mPas. Then 16 g of a lipase enzyme concentrate from Pseudomonas sp. with an activity of 5 000 LCA/mg (for definition and determination of LCA-units c.f. Seměriva, Biochem. 10, 2143 (1971) are added and the mixture is dispersed for another 10 minutes. One obtains a liquid enzyme formulation with an activity of 80 LCA/mg, which after 6 weeks at 25° C. does not show any creaming or settling. The activity of the formulation was found to be 77–78 LCA/mg.

EXAMPLE L

Saponification of beef suet 400 g of beef suet and 600 g of water are emulsified with 5 g of the lipase preparation of Example K at 50° C. and the emulsion is stirred at this temperature for 3 hours. Then the proportion of fatty acids liberated in the process of saponification is determined by titration according to IUPAC-standard, Methods of Oils, Fats and Derivates, 6th Ed., pg. 56, Pergamon Press, Oxford (1979). The degree of hydrolysis was found to be 72%.

EXAMPLE M

Preparation of a liquid cellulase-hemicellulase formulation 882 g of ethylene glycol *, 13 g of fumed silica (Aerosil 200 ®, product of Hoechst AG, W.-Germany) and 5 g of a surface active agent based on modified fatty acid (Borchigen STL ®, product of Borchers GmbH, Goslar) are dispersed in a stirring vessel using a toothed-disk agitator at a rotative speed of 15–18 m/sec for 10 minutes. The viscosity of the system rises from 35 mPas to 330 mPas. Then 100 g of an enzyme concentrate of cellulase/hemicellulase from *Trichoderma viride* with an activity of 10 000 FPU/g (FPU units as defined by M. Mandels, R. Andreotti and C. Roche, Biotech. Bioeng. Sym. 6, 17 (1976) are added and are dispersed for another 10 minutes. One obtains a viscous, homogeneous enzyme preparation (viscosity 2 600 mPas) with an activity of 1 000 FPU/g), which after 5 weeks' storing at 25° C. shows no sign of settling or creaming.

EXAMPLE N

Use of cellulase-hemicellulase formulation in gluten filtration 10 kg of a gluten suspension (dry matter contents about 30%) which was separated from corn starch by centrifugation is treated with 3 g of the cellulase preparation according to example M at 40° C. for one hour. Polysaccharides which interfere with filtration have been degraded by then. Better and quicker filterability on the vacuum rotational filter ensues.

EXAMPLE O 975 g of glycerol * (water content <1% ) and 20 g of fumed silica (Aerosil 380 ® of Degussa AG, W.-Germany) are dispersed in a stirring vessel using a toothed-disk agitator at a rotative speed of 15–18 m/sec for 15 minutes. Then 5 g of a pectinase concentrate from Aspergillus oryzae with an activity of 100 000 PGU/mg are added and the mixture is dispersed for another 10 minutes.(For definition and measurement of PGU c.f. Röhm-Analysen-vorschrift PZV-30). In this way a liquid, homogeneous, readily pourable pectinase formulation with 5 000 PGU/mg is obtained, which after storing at 25° C. for 6 weeks shows neither creaming nor settling. The activity after this period of time was found to be 97% of the original activity.

EXAMPLE P 1 000 l of freshly pressed apple juice are treated with 50 g of the pectinase formulation according to example 0. This causes degradation of pectin as well as of colloidal substances among the turbidifying material present. Those colloids would interfere with settling and further clarification via ultrafiltration or microfiltration. After 2 hours of treatment, settling is carried out by adding bentonite. Subsequent filtration is performed easily and without any problem.

EXAMPLE Q

Liquid enzyme composition for the soaking of hides and skins

In vessel, 300 g of (1) a nonionic surfactant made of $C_{13}$-oxoalcohol condensed with 6 moles of ethylene oxide and 682 g of a nonionic surfactant made of $C_{13}$-oxoalcohol, (2) 9 mol of ethylene oxide, (3) 13 g of Aerosil380 ® (fumed silica, product of Degussa AG, W.-Germany), and (4) 5 g of Borchigen STL ® a surface active agent are dispersed with a toothed-disk agitator at a rotative speed of 15–18 m/s for 15 minutes. Then 27.5 g of an alkaline protease from *Bacillus subtilis* (activity 80 000 LVE/g) and 10 g of a fungal protease from *Aspergillus parasiticus* (activity 220 000 LVE/g) are added in this order and are dispersed for another 10 minutes. One obtains a liquid, homogenous enzyme preparation which can be easily transferred by pouring or pumping and which has not settled or creamed after 4 weeks. The activity after this period of time at 15° C. is 96% of the original one, which was 4 400 LVE/g.

EXAMPLE R

Enzymatic soaking of presoaked cattle hide (percentage figures given refer to the weight of the skin materials treated (salt weight)

100 kg of presoaked cattle pelts
200% of water (26° C.)
0.25% of the enzyme composition of example Q
0.2% of sodium hydroxide solution (50% water)

After 5 hours of soaking in a vat, the salted cattle pelts are thoroughly softened. Most of the grease and scud is removed and the skin is ready for hair loosening.

EXAMPLE S

Liquid bating preparation with deliming and defatting effect 400 g of ethylene carbonate, 300 g of methyl ethylketone and 264 of nonionic surfactant ($C_{16}$–$C_{18}$ fatty alcohol condensed with 9 moles ethylene oxide) are mixed and warmed to 40° C. in a stirring vessel. Then 10 g of fumed silica (Aerosil 380 ®) and 6 g of Borchigen STL ® (see example Q) are added. The mixture is dispersed by means of a toothed-disk agitator at 15–18 m/sec for 15 minutes. The viscosity rises from 60 mPas to 1040 mPas. Then 20 g of pancreatic enzyme concentrate (activity 40 000 LVE/g) are added and the mixture is dispersed for another 20 minutes. One obtains a liquid homogeneous enzyme formulation which is easily poured and which will neither settle nor cream during 5 weeks of storing at 25° C. Activity after this period was found to be 760 LVE (Original activity was 800 LVE/g).

EXAMPLE T

Enzymatic bating and deliming of cattle pelts (percentages refer to the weight of pelt material)

10 kg of limed and washed cattle split pelts, 3–4 mm thick are treated with 30% of water at 35° C., 1% of the enzyme formulation according to example S (800 LVE/g) and 2 g of ammonium sulfate. After 70 minutes the pelts are thoroughly delimed and the scud is well loosened. The final pH value of the liquid was found to be 7.8. The natural grease is widely removed from the skin and is emulsified in the liquor.

EXAMPLE U 984 g of 1,2-propylene glycol * (anhydrous) are dispersed with 10 g of fumed silica (Aerosil 380 ®) and 5 g of a surface active agent (Borchigen STL ®) for 10 minutes by means of a toothed-disk agitator at 15–18 m/s in a beaker. The viscosity of the liquid rises from 20 mPas to 310 mPas. Then 1 g of horseradish peroxidase (activity 1000 units/g; for definition and determination cf. F.W.J. Toele, Biochem. Biophys. Acta 35, 543 [1959] are added and the mixture is dispersed for another 10 minutes. A liquid, readily flowable enzyme formulation is obtained (280 mPas) which after four weeks of storage at room temperature showed neither settling nor creaming. The activity was reduced by about 2% compared with the original enzyme activity.

EXAMPLE V

Preparation of a dye solution (model reaction)
solution a)

1 g of m-phenylene diamine are dissolved in 999 g of 0.1 molar phosphate buffer (pH=7).

solution b) 0.35 g of hydrogen peroxide (30%)

Enzymatic oxidation process 1 g of the peroxidase formulation according to Example U are dissolved in 1000 g of solution a). 5 g of solution b) are added with stirring. Formation of a red azo dye is observed, whose colour has become quite intense after some minutes.

We claim:

1. A method for enzymatic deliming and bating of pelts in a bath which comprises the step of contacting said pelts with a liquid formulation comprising at least one enzyme dispersed in a substantially anhydrous organic liquid, said liquid consisting essentially of 5 or 6 membered cyclic carbonate ester as a liquid carrier vehicle therefor with from 0.1 to 6 percent, by weight of said organic liquid, of a finely divided solid inorganic dispersing agent.

2. A method as in claim 1 wherein said liquid formulation comprises a pancreatic enzyme.

3. A method for the enzymatic soaking of hides and skins in a both which comprises the step of contacting said hides and skins with a liquid formulation comprising at least one enzyme dispersed in a substantially anhydrous organic liquid, said liquid consisting essentially of 5 or 6 membered cyclic carbonate ester as a liquid carrier vehicle therefor with from 0.1 to 6 percent, by weight of said organic liquid, of a finely divided solid inorganic dispersing agent.

4. A method as in claim 3 wherein said liquid formulation comprises a neutral protease.

5. A method for the enzymatic degreasing of pelts wherein the enzyme in supplied as a liquid formulation comprising at least one enzyme dispersed in a substantially anhydrous organic liquid said liquid consisting essentially of 5 or 6 membered cyclic carbonate ester as a liquid carrier vehicle therefor with from 0.1 to 6 percent, by weight of said organic liquid, of a finely divided solid inorganic dispersing agent.

6. A method as in claim 5 wherein said liquid formulation comprises a protease derived from an *Aspergillus* species.

* * * * *